United States Patent [19]

Hasegawa et al.

[11] Patent Number: 4,675,184

[45] Date of Patent: Jun. 23, 1987

[54] PHARMACEUTICAL COMPOSITION CONTAINING INTERFERON IN STABLE STATE

[75] Inventors: Kenji Hasegawa, Ibaraki; Yasuo Sakano, Amagasaki; Yasuhiro Katsuragi; Kenji Aimoto, both of Toyonaka; Kunio Sugihara, Otsu, all of Japan

[73] Assignees: 501 Sunstar Kabushiki Kaisha, Takatsuki; 502 Toray Industries, Inc., Tokyo, both of Japan

[21] Appl. No.: 568,033

[22] Filed: Jan. 4, 1984

Related U.S. Application Data

[63] Continuation-in-part of Ser. No. 443,620, Nov. 22, 1982, abandoned.

[30] Foreign Application Priority Data

Nov. 28, 1981 [JP] Japan ............................ 56-191250
Nov. 28, 1981 [JP] Japan ............................ 56-191251
Nov. 28, 1981 [JP] Japan ............................ 56-191252
Nov. 28, 1981 [JP] Japan ............................ 56-191253
Mar. 27, 1982 [JP] Japan ............................ 57-049444

[51] Int. Cl.$^4$ ............................................. A61K 45/02
[52] U.S. Cl. ...................................... 424/85; 435/811
[58] Field of Search ......................................... 424/85

[56] References Cited

U.S. PATENT DOCUMENTS

| 3,981,991 | 9/1976 | Stewart et al. | 424/85 |
| 4,100,150 | 7/1978 | Cartwright | 424/85 |
| 4,137,307 | 1/1979 | Funakoshi et al. | 424/177 |
| 4,252,791 | 2/1981 | Grossberg et al. | 424/85 |

FOREIGN PATENT DOCUMENTS 102519 8/1980 Japan .
164630 12/1980 Japan .

OTHER PUBLICATIONS

International Publication No. WO83/0119, Publication Date 4/14/83.

*Primary Examiner*—Blondel Hazel

[57] ABSTRACT

A pharmaceutical composition for treating viral diseases, such as pasta, gargle, gel, ointment, suppository, spray, etc., containing interferon in a stable state which comprises an effective amount of human interferon, 15 to 60% by weight of a tri or higher polyhydric sugar alcohol and an organic acid buffer as stabilizers, and a conventional pharmaceutical carrier or diluent. The pH of the composition is about 3 to 6. Optionally, the composition can further contain as a stabilizer an anionic surfactant and/or albumin.

13 Claims, No Drawings

PHARMACEUTICAL COMPOSITION CONTAINING INTERFERON IN STABLE STATE

This application is a continuation-in-part application of pending application Ser. No. 443,620 filed Nov. 22, 1982 now abandoned.

The present invention relates to a pharmaceutical composition containing interferon in a stable state.

It has been known that interferon is a certain kind of protein having anti-virus activity produced by stimulation of animal cells with viruses, double-stranded ribonucleic acids (RNA), etc. and has animal species specificity in its activity.

Recently, it has become apparent that interferon derived from human cells or human interferon gene-recombining microbial cells shows therapeutic effects on various human diseases and clinical application thereof has been tried.

In view of the therapeutic effects of interferon, it has been expected that interferon can be used as an active ingredient of various drugs. However, interferon is a fairly unstable material and, particularly, clinically applicable refined interferon readily decreases its activity and is readily inactivated by elevated temperatures, mechanical treatments such as shaking, freezing or filtration and the like. Therefore, even if interferon is formulated in a composition, interferon can hardly exert its effect unless stabilization thereof is effected.

In order to obtain a pharmaceutical composition containing human interferon in a stable state, the present inventors have intensively studied and have surprisingly found that, when a certain kind of materials is present in a composition, stability of human interferon is remarkably improved.

The main object of the present invention is to provide a pharmaceutical composition for treating viral diseases containing as an active ingredient human interferon in a stable state.

This object as well as other objects and advantages of the present invention will become apparent to those skilled in the art from the following description.

According to the present invention, there is provided a pharmaceutical composition for treating viral diseases containing interferon in a stable state which comprises an effective amount of human interferon, a polyhydric (tri or higher) sugar alcohol and an organic acid buffer as stabilizers, and a conventional pharmaceutical carrier or diluent. Optionally, in addition to the sugar alcohol and the organic acid buffer, the composition of the present invention can further contain as a stabilizer a material selected from the group consisting of anionic surfactants, albumin and combinations thereof. The composition of the present invention can be prepared in various forms suitable for application in the oral cavity, topical application to the skin, rectal, vaginal and urethral administration, application to the eye, the nose and the throat, etc. and interferon in the composition can maintain its activity for a long period of time.

Interferon to be formulated in the composition of the present invention can be any interferon derived from human being. For example, there can be used interferon prepared by using human leukocytes or normal human diploid cells according to a known technique, interferon derived from human interferon gene-recombining microbial cells prepared according to a known recombination deoxyribonucleic acid (DNA) technique or interferon prepared by using a know cellfusion technique.

The amount of interferon to be formulated in the composition is not limited to a specific one and can be appropriately chosen based on a desired effect, a particular form of the composition and the like. However, generally, in view of the effect, it is preferable to formulate interferon having the specific activity of $1 \times 10^5$ international units (IU)/mg protein or more in an amount of $1 \times 10^4$ IU or more per 100 g of the composition.

Examples of the polyhydric sugar alcohols to be used as the stabilizer in the present invention are those of trihydric or higher such as glycerin, erythritol, xylitol, sorbitol and mannitol. These polyhydric sugar alcohols can be used alone or in a combination thereof. In view of stabilization of interferon, the sugar alcohol is formulated in an amount of 15% by weight or more, preferably, 25 to 60% by weight based on the composition.

The organic acid buffers to be used as the stabilizer in the present invention can be conventional buffers of organic acids and salts thereof such as citrate buffers (e.g. monosodium citrate-disodium citrate mixture, citric acid-trisodium citrate mixture, citric acid-monosodium citrate mixture, etc.), succinate buffers (e.g. succinic acid-monosodium succinate mixture, succinic acid-sodium hydroxide mixture, succinic acid-disodium succinate mixture, etc.), tartrate buffers (e.g. tartaric acid-sodium tartrate mixture, tartaric acid-potassium tartrate mixture, tartaric acid-sodium hydroxide mixture, etc.), fumarate buffers (e.g. fumaric acid-monosodium fumarate mixture, fumaric acid-disodium fumarate mixture, monosodium fumarate-disodium fumarate mixture, etc.) gluconate buffers (e.g. gluconic acid-sodium gluconate mixture, gluconic acid-sodium hydroxide mixture, gluconic acid-potassium gluconate mixture, etc.), oxalate buffers (e.g. oxalic acid-sodium oxalate mixture, oxalic acid-sodium hydroxide mixture, oxalic acid-potassium oxalate mixture, etc.), lactate buffers (e.g. lactic acid-sodium lactate mixture, lactic acid-sodium hydroxide mixture, lactic acid-potassium lactate mixture, etc.) and acetate buffers (e.g. acetic acid-sodium acetate mixture, acetic acid-sodium hydroxide mixture, etc.). It is noteworthy that inorganic acid buffers such as phosphate buffers do not improve the stability of interferon. The organic acid buffer is formulated in an amount of 0.01 mole/kg composition or more, preferably, 0.1 to 0.2 mole/kg composition so as to adjust to pH about 3 to 6.

Examples of the anionic surfactants are sodium alkyl sulfates, alkyl groups of which have 8 to 18 carbon atoms (e.g. sodium lauryl sulfate, sodium oleyl sulfate, etc.) sodium polyoxyethylene alkyl ether sulfates, average number of moles of ethylene oxide added of which are 2 to 4 and alkyl groups of which have 8 to 18 carbon atoms (e.g. sodium polyoxyethylene lauryl ether sulfate, sodium polyoxyethylene oleyl ether sulfate, etc.) and sodium alkyl sulfosuccinates alkyl groups of which have 8 to 18 carbon atoms (e.g. sodium lauryl sulfosuccinate, sodium oleyl sulfosuccinate, etc.). It is noteworthy that, among various surfactants, only anionic surfactants can improve the stability of interferon. The anionic surfactants can be used alone or in a combination thereof and are formulated in an amount of 0.008% by weight or more, preferably, 0.05% to 4% by weight or more, particularly, 0.1 to 1% by weight based on the composition.

Examples of albumin are human serum albumin, bovine serum albumin, ovalbumin and a mixture thereof.

Albumin is formulated in an amount of 0.01 to 1% by weight based on the composition.

The pharmaceutical carrier or diluent to be used in the present invention can be solid or liquid. For example, there can be used waxes, cellulose derivatives, carboxyvinyl polymers and water. It has been found that sodium carboxymethyl cellulose is particularly preferred because it does not adversely affect on the activity of interferon.

The composition of the present invention can be prepared in a conventional form known in the fields of drugs such as pasta and gargle for application in the oral cavity, gel and ointment for topical application to the skin, gel and suppository for rectal, vaginal and urethral administration and liquid, gel, ointment and spray for application to the eye, the nose and the throat by incorporating the stabilizer and the carrier or diluent with interferon according to a conventional technique. In order to avoid decrease of the activity of interferon during the manufacturing steps, it is preferable to add interferon to a mixture of remaining ingredients at the end step.

The other ingredient(s) are not specified unless they affect on the activity of interferon and conventional ingredients such as perfumes, sweeteners, etc. can be used.

The following Experiments and Examples further illustrate the present invention in detail but are not to be construed to limit the scope thereof. Interferon used in the Experiments and Examples was obtained from fibroblasts derived from human prepuce by the supperinduction method (Tan, Y. H., Armstrong, J. A., Ke, Y.H. and Ho, M. (1970), Proc. Natl. Acad. Sci., 67, 464; and Vilcek, J. (1970), J. Gen. Viol., 56, 76). The activity of interferon was measured by using Sindbis virus and a cell line derived from human amnion (FL cells) according to the cytopathogenic effect (CPE) method (Havell, E. A. and Vilcek, J. (1972), antimicrob. Agents Chemother., 2, 476; Oie, H. K., (1977), Texas Rep. Biol. Med., 35, 154). The activity thus measured was compared with that of standard interferon measured at the same time and was expressed in international units (IU).

EXPERIMENT 1

Lyophilized interferon ($1 \times 10^6$ IU) was restored by adding a physiological saline solution (1 ml) and was diluted with a physiological saline solution to obtain a interferon solution ($1 \times 10^5$ IU/ml). The interferon solution (0.1 ml) was mixed with physiological saline solution (0.9 ml) containing the sugar alcohol shown in Table 1 and allowed to stand at 45° C. for 24 hours. After 24 hours, the activity of interferon in the mixture was measured and the rate of remaining activity (%) was calculated by taking the initial activity as 100%. The results as well as the sugar alcohols used and the concentration thereof are shown in Table 1.

TABLE 1

| Sugar Alcohols | Concentrations (wt. %) | Rate of remaining activity (%) |
|---|---|---|
| Glycerin | 45 | 100 |
| Glycerin | 27 | 17 |
| Glycerin | 10 | 8 |
| Glycerin | 2 | 7 |
| Xylitol | 45 | 70 |
| Sorbitol | 45 | 30 |
| Mannitol | 45 | 50 |
| Erythritol | 45 | 88 |
| Control (without addition of any sugar alcohol) | — | 0 |

TABLE 1-continued

| Sugar Alcohols | Concentrations (wt. %) | Rate of remaining activity (%) |
|---|---|---|

EXPERIMENT 2

The same procedure as described in Experiment 1 was repeated except that the mixture was allowed to stand at 37° C. for 1 month or 4° C. for 6 months. The results are shown in Table 2.

TABLE 2

| Sugar alcohols | Concentrations (wt. %) | Rate of remaining activity (%) 37° C., 1 month | Rate of remaining activity (%) 4° C., 6 months |
|---|---|---|---|
| Glycerin | 45 | 80 | 95 |
| Xylitol | 45 | 60 | 80 |
| Sorbitol | 45 | 25 | 30 |
| Mannitol | 45 | 42 | 70 |
| Erythritol | 45 | 70 | 90 |
| Control (without addition of any sugar alcohol) | — | 0 | 8 |

As shown in Tables 1 and 2, all the sugar alcohols used, particularly, glycerin, xylitol and erythritol improve stability of interferon.

EXPERIMENT 3

The interferon solution as prepared in Experiment 1 (0.1 ml) was mixed with an aqueous solution (0.9 ml) containing the buffer shown in Table 3 and was allowed to stand with shaking (170 r.p.m.) at 37° C. for 24 hours. After 24 hours, the activity of interferon in the mixture was measured and the rate of remaining activity (%) was calculated according to the same manner as in Experiment 1. The results are shown in Table 3.

TABLE 3

| Buffers | Concentrations (mole/liter) | pH | Rate of remaining activity (%) |
|---|---|---|---|
| Phosphate buffer | 0.1 | 6 | 4 |
| Phosphate buffer | 0.1 | 7 | 8 |
| Phosphate buffer | 0.1 | 8 | 6 |
| Citrate buffer | 0.1 | 4 | 79 |
| Citrate buffer | 0.1 | 5 | 75 |
| Citrate buffer | 0.1 | 6 | 53 |
| Control (distilled water) | — | 6 | 0 |

EXPERIMENT 4

The interferon solution as prepared in Experiment 1 (0.1 ml) was mixed with an aqueous solution (0.9 ml) containing the surfactant shown in Table 4 and was allowed to stand at 45° C. for 24 hours. After 24 hours, the activity of interferon in the mixture was measured and the rate of remaining activity (%) was calculated according the same manner as in Experiment 1. The results are shown in Table 4.

TABLE 4

| Surfactants | Concentrations (wt. %) | Rate of remaining activity (%) |
|---|---|---|
| Sodium lauryl sulfate (anionic surfactant) | 1 | 94 |
| | 0.2 | 92 |
| | 0.04 | 52 |
| | 0.008 | 40 |
| | 0.0016 | 4 |
| Polyoxyethylene sorbitan fatty acid ester (nonionic surfactant)* | 1 | 7 |
| | 0.2 | 7 |
| | 0.04 | 6 |
| Polyoxyethylene hardened castor oil derivative (nonionic surfactant)** | 1 | 5 |
| | 0.2 | 6 |
| | 0.04 | 5 |
| Control (distilled water) | — | 5 |

*Tween 80 manufactured by Atlas Powder Co. in U.S.A.
**Nikkol HCO-60 manufactured by Nikko Chemical Co., Ltd. in Japan

EXPERIMENT 5

The same procedure as described in Experiment 4 was repeted by using various anionic surfactants. The results are shown in Table 5.

TABLE 5

| Surfactants | Concentrations (wt. %) | Rate of remaining activity (%) |
|---|---|---|
| Sodium lauryl sulfate | 0.2 | 98 |
| Sodium polyoxyethylene stearyl ether sulfate | 0.2 | 100 |
| Sodium lauryl sulfosuccinate | 0.2 | 95 |
| Sodium polyoxyethylene lauryl ether sulfate | 0.2 | 98 |
| Control (distilled water) | — | 8 |

As shown in Tables 4 and 5, the anionic surfactants improve stability of interferon, whereas the nonionic surfactants do not improve stability of interferon.

EXAMPLE 1

According to the following formulation, various topical pastas were prepared.

| Ingredients | % by weight |
|---|---|
| Cetanol | 2.0 |
| Glyceryl monostearate | 9.27 |
| Tween 80 | 2.0 |
| Hydroxyethyl cellulose | 5.5 |
| Saccharin | 0.09 |
| Sugar alcohol (shown in Table 6) | 40.0 |
| Citrate buffer (pH 4.5, 0.4 mole/liter distilled water) | 25.0 |
| Distilled water | up to 100% |

The above ingredients were mixed and to the mixture was added an interferon sulution prepared as in Experiment 1 in an amount of $1 \times 10^7$ IU/100 g product. The resulting mixture was thoroughly mixed to obtain an interferon-containing dental pasta.

The dental pasta thus obtained was allowed to stand at 37° C. for 1 month or at 4° C. for 6 months. After this period, the activity of interferon in the pasta was measured and the rate of remaining activity (%) was calculated by taking the initial activity as 100%. The results are shown in Table 6.

TABLE 6

| Sugar alcohols | Rate of remaining activity (%) | |
|---|---|---|
| | 37° C., 1 month | 4° C., 6 months |
| Glycerin | 88 | 92 |
| Erythritol | 70 | 86 |
| Arabitol | 65 | 58 |
| Mannitol | 58 | 78 |
| Control (substituted distilled water for sugar alcohol) | 22 | 64 |

EXAMPLE 2

According to the same procedure as described in Example 1, dental pastas were prepared and the rates of remaining activity (%) of interferon were calculated after storage at 37° C. for 1 month and 4° C. for 6 months. The formulations and the results are shown in Table 7.

TABLE 7

| Ingredients | % by weight | | |
|---|---|---|---|
| | 1 | 2 | 3 |
| Sodium carboxymethyl cellulose | 2.0 | 2.0 | 2.0 |
| Glycerin | 45.0 | 30.0 | 20.0 |
| Sodium lauryl sulfate | 0.2 | 0.2 | 0.2 |
| Citrate buffer (pH 4.5, 0.4 mole/liter distilled water) | 25.0 | 25.0 | 25.0 |
| Distilled water | up to 100% | up to 100% | up to 100% |
| Interferon | $1 \times 10^7$ IU/100 g product | $1 \times 10^7$ IU/100 g product | $1 \times 10^7$ IU/100 g product |
| Rate of remaining activity (%) | | | |
| 37° C., 1 month | 85 | 82 | 60 |
| 4° C., 6 months | 96 | 94 | 77 |

EXAMPLE 3

According to the following formulation, a gargle was prepared.

| Ingredients | % by weight |
|---|---|
| Organic acid buffer (shown in Table 8, 0.2 mole/liter distilled water; pH 4.5) | 50.0 |
| Glycerin | 25.0 |
| Saccharin | 0.02 |
| Perfume | 0.02 |
| Distilled water | up to 100% |
| Interferon | $1 \times 10^6$ IU/100 g product |

The above ingredients were mixed and to the mixture was added an interferon solution prepared as in Experiment 1 in an amount of $1 \times 10^6$ IU/100 g product. The resulting mixture was thoroughly mixed to obtain an interferon-containing gargle.

The gargle thus obtained was allowed to stand at 37° C. for 1 month or at 4° C. 6 months. After this period, the remining activity of interferon was measured and the rate of remaining activity (%) was measured by taking the initial activity as 100%.

The results are shown in Table 8.

TABLE 8

| Organic buffers | Rate of remaining activity (%) | |
|---|---|---|
| | 37° C., 1 month | 4° C., 6 months |
| Citrate buffer | 64 | 92 |
| Succinate buffer | 60 | 90 |
| Tartrate buffer | 48 | 82 |
| Fumarate buffer | 44 | 70 |
| Gluconate buffer | 38 | 76 |
| Oxalate buffer | 40 | 72 |
| Lactate buffer | 64 | 84 |
| Acetate buffer | 66 | 90 |
| Control (without buffer) | 10 | 32 |

EXAMPLE 4

According to the following formulation, a gel for topical application to the skin was prepared by a standard technique provided that an interferon solution prepared as in Experiment 1 was added at the end step.

| Ingredients | % by weight |
|---|---|
| Sugar alcohol (shown in Table 9) | 45.0 |
| Tween 80 | 0.2 |
| Carbopol 940 (carboxyvinyl polymer manufactured by B. F. Goodrich Co. in U.S.A.) | 2.0 |
| Distilled water | up to 100% |
| Interferon | $1 \times 10^7$ IU/100 g product |

The interferon-containing gel thus obtained was allowed to stand at 37° C. for 1 month or at 4° C. for 6 months. After this period, the remaining activity of interferon was measured and the rate of remaining activity (%) was calculated by taking the initial activity as 100%.

The results are shown in Table 9.

TABLE 9

| Sugar alcohols | Rate of remaining activity (%) | |
|---|---|---|
| | 37° C., 1 month | 4° C., 6 months |
| Glycerin | 80 | 88 |
| Erythritol | 76 | 80 |
| Arabitol | 70 | 64 |
| Mannitol | 40 | 76 |
| Control (substituted distilled water for sugar alcohol) | 0 | 1 |

EXAMPLE 5

According to the same procedure as described in Example 4, an interferon-containing gel for topical application to the skin of the following formulation.

| Ingredients | % by weight |
|---|---|
| Glycerin | 45 |
| Sodium carboxymethyl cellurose | 2 |
| Sodium lauryl sulfate | 0.2 |
| Citrate buffer (pH 4.5, 0.4 mole/liter distilled water) | 25.0 |
| Distilled water | up to 100% |
| Interferon | $1 \times 10^6$ IU/100 g product |

When the gel was allowed to stand at 37° C. for 1 month or at 4° C. for 6 months, the rate of remaining activity (%) of interferon was 70% after storage at 37° C. for 1 month and 90% after storage at 4° C. for 6 months. When glycerin, sodium lauryl sulfate and citrate buffer in the above formulation were substituted for distilled water, the rate of remaining activity (%) of interferon in the resulting gel was 0% after storage at 37° C. for 1 month and 1% after storage at 4° C. for 6 months.

EXAMPLE 6

According to the same procedure as described in Example 4, a topical gel of the following formulation was prepared.

| Ingredients | % by weight |
|---|---|
| Glycerin | 45.0 |
| Sodium carboxymethylcellulose | 2.0 |
| Human serum albumin | 0.3 |
| Citrate buffer (pH 4.5, 0.4 mole/liter distilled water) | 25.0 |
| Distilled water | up to 100% |
| Interferon | $1 \times 10^6$ IU/100 g product |

When the topical gel was allowed to stand at 37° C. for 1 month or at 4° C. for 6 months, the rate of remaining activity of interferon was 74% after storage at 37° C. for 1 month and 96% after storage at 4° C. for 6 months. When glycerin, albumin, citrate buffer in the above formulation were substituted for distilled water, the rates of remaining activity at both 37° C. for 1 month and 4° C. for 6 months were 0%'s, respectively.

EXAMPLE 7

According to the same procedure as described in Example 4, a topical gel of the following formulation was prepared and the rate of remaining activity (%) of interferon was calculated after storage at 37° C. for 1 month or at 4° C. for 6 months.

| Ingredients | % by weight |
|---|---|
| Tween 80 | 0.2 |
| Carbopol 940 | 2.0 |
| Glycerin | 30.0 |
| Organic acid buffer (shown in Table 10, 0.2 mole/liter distilled water; The final pH was adjusted to 5.0) | 50.0 |
| Distilled water | up to 100% |
| Interferon | $1 \times 10^6$ IU/100 g product |

The results are shown in Table 10.

TABLE 10

| Organic buffers | Rate of remaining activity (%) | |
|---|---|---|
| | 37° C., 1 month | 4° C., 6 months |
| Citrate buffer | 48 | 94 |
| Succinate buffer | 44 | 90 |
| Tartrate buffer | 38 | 90 |
| Fumarate buffer | 32 | 90 |
| Gluconate buffer | 30 | 76 |
| Oxalate buffer | 46 | 82 |
| Lactate buffer | 40 | 88 |
| Acetate buffer | 44 | 90 |
| Control (without buffer) | 28 | 44 |

EXAMPLE 8

According to the same procedure as described in Example 4, a topical gel of the formulation shown in Table 11 was prepared and the rate of remaining activity (%) of interferon was calcuted after storage at 37°

C. for 1 month or at 4° C. for 6 months. The results are shown in Table 11.

TABLE 11

| Ingredients | % by weight | | | |
|---|---|---|---|---|
| | 1 | 2 | 3 | 4 |
| Sodium lauryl sulfate | 0.2 | 0.04 | 0.008 | 0 |
| Glycerin | 15 | 15 | 15 | 15 |
| Sodium carboxy-methyl cellulose | 2 | 2 | 2 | 2 |
| Citrate buffer (pH 4.5, 0.4 mole/liter distilled water) | 25 | 25 | 25 | 25 |
| Distilled water | up to 100% | up to 100% | up to 100% | up to 100% |
| Interferon | 1 × 10⁷ IU/100 g product | 1 × 10⁷ IU/100 g product | 1 × 10⁷ IU/100 g product | 1 × 10⁷ IU/100 g product |
| Rate of remaining activity (%) | | | | |
| 37° C., 1 month | 66 | 65 | 50 | 16 |
| 4° C., 6 months | 94 | 90 | 80 | 42 |

EXAMPLE 9

According to the following formulation, an interferon-containing suppository was prepared by mixing Macrogol 400, glycerin, an organic acid buffer and sodium lauryl sulfate and adding thereto an interferon solution prepared as in Experiment 1. After the resulting mixture was thoroughly mixed, it was put into a container, cooled and shaped and each 1 g portion thereof was filled into a capsule.

| ingredients | % by weight |
|---|---|
| Macrogol 400 | 50 |
| Glycerin | 35 |
| Organic acid buffer (shown in Table 12, 0.1 mole/liter aqueous solution; pH 5.0) | 15 |
| Sodium lauryl sulfate | 0.2 |
| Interferon | 1 × 10⁶ IU/g mixture |

The suppository thus obtained was allowed to stand at 37° C. for 1 month or at 4° C. for 6 months. After this period, the remaining activity of interferon was measured and the rate of remaining activity (%) of interferon was calculated by taking the initial activity as 100%.

The results are shown in Table 12.

TABLE 12

| Organic acid buffers | Rate of remaining activity (%) | |
|---|---|---|
| | 37° C., 1 month | 4° C., 6 months |
| Citrate buffer | 76 | 82 |
| Succinate buffer | 70 | 76 |
| Tartrate buffer | 64 | 68 |
| Fumarate buffer | 66 | 74 |
| Gluconate buffer | 50 | 66 |
| Oxalate buffer | 60 | 64 |
| Lactate buffer | 68 | 76 |
| Acetate buffer | 54 | 76 |
| Control (without buffer) | 32 | 46 |

EXAMPLE 10

According to the following formulation, a spray type composition was prepared.

| Ingredients | % by weight |
|---|---|
| Dimethyl ether | 60 |
| Glycerin | 18 |
| Citrate buffer (pH 4.5, 0.1 mole/liter distilled water) | up to 100% |
| Interferon | 1 × 10⁶ IU/g mixture |

The above ingredients other than interferon were mixed and to the mixture was added the interferon in the form of the solution prepared as in Experiment 1. When the spray type composition was allowed to stand at 37° C. for 1 month or at 4° C. for 6 months, the rate of remaining activity of interferon was 24% after storage at 37° C. for 1 month and 72% after storage at 4° C. for 6 months. When glycerin in the above formulation was substituted for citrate buffer, the rate of remaining activity of the resulting composition was 4% after storage at 37° C for 1 month and 12% after storage at 4° C. for 6 months.

What is claimed is:

1. A pharmaceutical composition for treating viral diseases containing interferon in a stable state which comprises an effective amount of human interferon, 15–60% by weight of glycerin, an organic acid buffer and a conventional pharmaceutical carrier or diluent, and pH of the composition being about 3 to 6.

2. A composition according to claim 1, wherein the organic acid buffer is a member selected from the group consisting of citrate buffer, succinate buffer, fumarate buffer, gluconate buffer, oxalate buffer, lactate buffer and acetate buffer and is formulated in an amount of 0.01 to 0.2 mole/kg composition.

3. A composition according to claim 1, wherein the composition further includes an anionic surfactant.

4. A composition according to claim 3, wherein the anionic surfactant is a member selected from the group consisting of sodium alkyl sulfate, the alkyl group of which has 8 to 18 carbon atoms; sodium polyoxyethylene alkyl ether sulfate, the average number of mole of ethylene oxide added of which is 2 to 4 and the alkyl group of which has 8 to 18 carbon atoms; sodium alkyl sulfosuccinte, the alkyl group of which has 8 to 18 carbon atoms; and a mixture thereof and is formulated in an amount of 0.008 to 4% by weight based on the composition.

5. A composition according to claim 1 or 3 in the form for application in the oral cavity.

6. A composition according to claim 1 or 3 in the form for topical application to the skin.

7. A composition according to claim 1 or 3 in the form for rectal administration.

8. A composition according to claim 1 or 3 in the form for vaginal administration.

9. A composition according to claim 1 or 3 in the form for urethral administration.

10. A composition according to claim 1 or 3 in the form for application to the eye.

11. A composition according to claim 1 or 3 in the form for application to the nose.

12. A composition according to claim 1 or 3 in the form for application to the throat.

13. A composition according to claim 1 or 3, wherein interferon having the specific activity of at least $1 \times 10^5$ IU/mg protein is formulated in an amount of at least $1 \times 10^4$ IU per 100 g of the composition.

* * * * *